Figure 1:
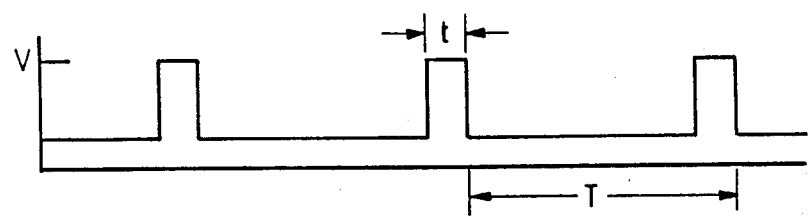

United States Patent [19]

Podsiadly et al.

[11] Patent Number: 4,817,331
[45] Date of Patent: Apr. 4, 1989

[54] METHOD AND APPARATUS FOR REMOVING EARTHWORMS FROM SOIL USING ELECTRIC PULSES

[75] Inventors: Paul Podsiadly, 50 Wilson Street, Woodstock, Ontario, Canada, M4S 3M5; Ian Soutar, London, Canada

[73] Assignee: Paul Podsiadly, Woodstock, Canada

[21] Appl. No.: 70,765

[22] Filed: Jul. 7, 1987

[30] Foreign Application Priority Data

Feb. 17, 1987 [CA] Canada .................................. 529940

[51] Int. Cl.⁴ .............................................. A01M 5/02
[52] U.S. Cl. .............................................. 47/1.3; 43/1
[58] Field of Search ...................... 47/1.3; 43/1; 119/1

[56] References Cited

U.S. PATENT DOCUMENTS 1,932,237 10/1933 Warner .
2,450,597 10/1948 Karnowski .
2,607,164 8/1952 Fenton .
2,770,075 11/1956 Moore .
3,763,593 10/1973 Guthrie .
3,793,770 2/1974 Johnson .
3,820,279 6/1974 Sieper .
3,973,354 8/1976 Schommer .

Primary Examiner—Robert A. Hafer
Assistant Examiner—Danton D. DeMille
Attorney, Agent, or Firm—Rogers, Bereskin & Parr

[57] ABSTRACT

A method and apparatus for causing earthworms to come to the surface of soil in which electric pulses are applied to the soil. The pulses are characterized by high power during a brief burst followed by a relatively long rest period. The method requires a small power supply and may therefore be put into practice with portable equipment.

16 Claims, 1 Drawing Sheet

U.S. Patent    Apr. 4, 1989    4,817,331

METHOD AND APPARATUS FOR REMOVING EARTHWORMS FROM SOIL USING ELECTRIC PULSES

This invention relates to a method and apparatus for causing earthworms to come to the surface of soil by passing electric pulses through the soil.

It is known to cause earthworms to come to the surface of soil by applying electricity to the soil and numerous devices have been proposed for this purpose. Previous devices, however, have commonly used a household type of voltage outlet or cumbersome storage battery of the type used in automobiles to generate the necessary voltage to remove the earthworms from the soil. Such devices have commonly been directed to novel safety features to prevent potentially fatal electric shocks from the power source used. Examples of these devices are disclosed in the following U.S. Pat. Nos.: 1,932,237 to Warner; 2,450,597 to Karnowski; 2,607,164 to Fenton; 2,770,075 to Moore; 3,763,593 to Guthrie; 3,793,770 to Johnson; 3,820,279 to Sieper; and 3,973,354 to Schommer.

These devices, however, suffer at least the following disadvanges.

(1) Since it is necessary that some part of an electrode or probe used to introduce the electricity to the soil have a naked contact with the soil, there is always some risk of a damaging electric shock to the operator.

(2) The devices have had limited portability by the need for a large battery or the need for proximity to a household voltage source.

(3) These devices, by using high power, fail to discriminate between large and small worms; and tend to damage the worms.

(4) Also, by using high power, the earthworms may be partially disabled, thus preventing them from reaching the surface of the earth, and thereby reducing the efficacy of the process.

It has not previously been appreciated that, as the applicants have found, earthworms may be removed from the soil by using a low voltage source which reduces the harmful effect of a shock, which allows the device to be readily portable, and which also discriminates in favour of large worms, and which allows earthworms to reach the surface without being immobilized or damaged.

This invention therefore provides in its broadest aspect a method of causing earthworms to come to the surface of the soil by applying to the soil electric pulses generated by a commercially available portable power source. The pulses are characterized by high power during a brief burst, with little or no power during the rest period between pulses, so that, on average, little power is consumed. In the preferred embodiment of the method, the pulses have the following characteristics:

average power, P, during the pulse between 10 watts and 500 watts; duration, t, between 0.1 seconds and 0.001 seconds; and frequency, f, between 0.5 Hertz and 10 Hertz; each of P, f and t chosen so that the product of P, f and t is maintained between 0.1 watts and 10 watts.

Preferred embodiments of the invention will now be described by way of example. In the figures, FIG. 1 is a graph showing typical pulses according to the invention; and FIG. 2 is a circuit diagram of a circuit for producing electric pulses according to the invention.

Figure 2:
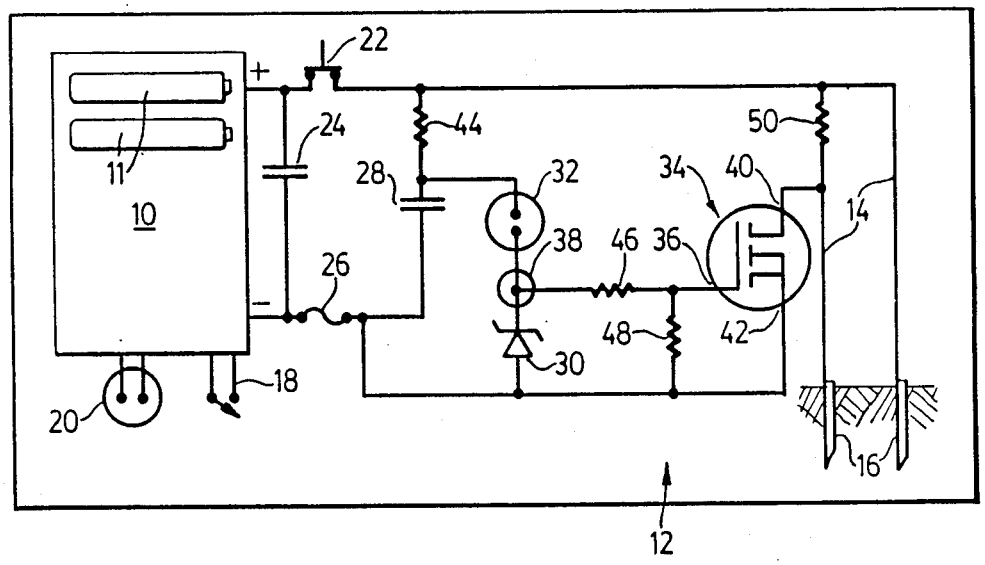

The applicants have found that earthworms may be caused to come to the surface of soil by applying to the soil electric pulses having certain characteristic waveforms. The pulses may have any shape (for example, sinusoidal, stepped or irregular) but the applicants have operated with a square wave pulse as shown in FIG. 1. Such a pulse may be defined by the following characteristics:

(1) Amplitude, which in this case is the voltage level of the top of the square wave (shown by the letter V in FIG. 1). For an irregular or rounded pulse, the average voltage during the pulse may be used instead to define the amplitude of the pulse.

(2) current, I, not shown in the figure, which is the current during the pulse;

(3) duration, which in this case is the time between the rise and fall of the pulse, as designated by t; and (4) frequency, designated by f, which is the reciprocal of the period shown by T in the figure.

The product of the instantaneous voltage and instantaneous current averaged for the duration of the pulse gives the average power (P) during the pulse. The applicants have found that a certain range of pulse characteristics provides an efficient and safe method of causing earthworms to come to the surface of soil without excessive power consumption, permitting use of, for example, "C" sized batteries.

If insufficient power is supplied, however, the efficacy of the method is reduced, and if the overall power consumption (including rest periods) is too great the operation of the method cannot be sustained for a reasonable length of time with portable equipment, since the current drain would then be too high for the power source.

The ranges that the applicants have found to be most preferable are as follows:

average power during the pulse between 10 watts and 500 watts;

pulse duration between 0.1 seconds and 0.001 seconds; and frequency between 0.5 Hertz and 10.0 Hertz, each of these ranges being further limited by being chosen so that the product of p, f and t is maintained between 0.1 watts and 10 watts.

At the higher overall power levels within the preferred ranges, power consumption becomes too high to achieve with small batteries and it is necessary to use more powerful batteries, thus reducing the portability of the equipment With average power beyond about 10 watts, car batteries or other similar high power sources are required.

At the lower overall power levels, near 0.1 watts, the efficacy overall average of the method becomes relatively poor, and good results are believed to be obtained with power above 0.5 watts and below 5 watts since between these ranges the average overall power is sufficient to cause the earthworms effectively to come to the surface (within the prefered range of duration and frequency) and yet is not too great a power drain on a readily portable power source.

Also, where the frequency becomes less than about 0.5 Hertz, the method is poor at inducing earthworms to leave the soil. At frequencies below about 0.5 Hertz, it is believed that the earthworms have time to escape out of the range of the electric pulses without going to the surface. If the frequency is too high, above about 10 Hertz, good results are not obtained. The applicants believe this is due to the earthworms being immobilized by the almost continuous bombardment of the electric shocks. This appears to be also true if DC or AC household type power supplies are used.

It is therefore preferable to have a frequency such that the earthworms have time to move between shocks without being able to move out of range of the shocks by going deeper into the ground.

The applicants have also found that if the pulse duration is greater than about 0.1 seconds, then the power is drained too quickly and if less than about 0.001 seconds, the earthworms are not easily removed, with essential failure of the method beyond those ranges.

The applicants have found that particularly good results are obtained when the average power during the pulse is between 30 watts and 300 watts, the duration of the pulse is about 0.05 seconds and the frequency is about 3 Hertz. Good results are also obtained where the duration is between 0.01 seconds and 0.004 seconds, and the frequency between 1 Hertz and 4 Hertz.

The voltage required of the power source is dependent upon the desired power and the expected current carrying capacity of the soil from which earthworms are to be removed. The current that passes through the soil is dependent on the size of the electrodes used to introduce the pulses to the soil and their location, and the resistivity of the soil.

If two electrodes are chosen, each about 2.5 mm. in diameter, 28 cm. long and placed 30 cm. apart, and the soil is moist, of the kind typically containing earthworms, then with a voltage source of 300 volts, the pulses having a square wave form with t=0.005 seconds and f=3 Hertz, the applicants have obtained a current during the pulse of about 0.34 amps. In this case, average power during the pulse is about 100 watts, with overall average power consumption about 1.5 watts.

The applicants have found that the current carrying capacity of moist soil does not vary greatly. With the parameters defined in the last preceding paragraph, the current does not vary beyond about 0.1 amps and 1 amp for a range of moist soils. Moist clay soils, particularly if saturated, are preferable because then the earthworms tend to gather near the surface of the soil. However, partly dry soil has been found to produce good results (if earthworms are present) by using smaller currents than used in wet soils. This is believed to be caused by the earthworms having high conductivity and therefore being the path of least resistance for the current in the soil. The earthworms are therefore affected by proportionally more of the current.

The waveform is believed to be irrelevant so long as the pulses have the appropriate high power. Thus the pulses need not be square, but may be, for example, stepped, sinusoidal, or irregular. Neither need the pulses be of uniform polarity. They may be positive or negative or any combination of positive and negative pulses.

Various means may be used to produced the desired pulse characteristics. We describe here with reference to FIG. 2 a particular device that uses commercially available "C" size batteries for the power source. The device the applicants have constructed consists of a small box (not shown) having a volume of about 300 cm.$^3$ which houses the power supply 10 and the components for the pulse generator (shown generally at 12). Two insulated power leads 14 extend out of the box and connect the pulse generator 12 to the ends of two electrodes 16. The design of the electrodes is a matter of choice, although the applicants have found that electrodes that are about 2.5 mm. in diameter, about 28 cm. long, and made of nickel or zinc plated steel work well. The top 6 cm. or so of the electrodes 16 are insulated to protect the operator while the electrodes 16 are inserted into the soil. Thin electrodes 16 are desirable to limit the current carried by the soil if it is very moist.

For the power supply 10, the applicants have used a commercially available 300 volt photoflash unit powered by two "C" size batteries shown for example at 11. It is desirable that the power supply 10 be capable of charging a 600 microfarad capacitor to 300 volts in about 30 seconds. The applicants have used for this purpose a photoflash unit manufactured by the Eastman Kodak Company of Rochester, N.Y., for use with the Kodak Instamatic camera. However, other photoflash units having the desired characteristics may be used. These units typically use a Xenon flash bulb and provide the desired voltage from two "C" sized batteries and a transistorized oscillator. The oscillator drives a transformer and the output of the transformer is passd through a diode to a capacitor where the charge is stored.

The power supply 10 is switched on by power supply switch 18 and the power supply neon light 20 goes on to show the power supply 10 is charged up (the neon light 20 goes on at about 270 volts).

The pulse generator 12 is activated by the push button switch 22 shown here connected to the positive pole of the power supply 10. The capacitor 24 connected across the power supply 10 is preferably either a 600 microfarad capacitor rated at 350 volts or two 300 microfarad capacitors also rated at 350 volts. The applicants have found that a single 300 microfarad capacitor will not work with the circuit shown here, but other equivalent capacitors or combinations of capacitors may be used.

A fast blow fuse 26 which is rated at 0.1 amps is connected to the negative pole of the power supply 10. A capacitor 28 is also connected in parallel with capacitor 24. Capacitor 28 is preferably a 0.5 microfarad capacitor rated at 200 volts. A Zener diode 30 is connected across the capacitor 28 in series with a neon light 32 which is chosen to be capable of discharging capacitor 28 in about 0.005 seconds. An Ne2 neon light is suitable for this purpose. Zener diode 30 is preferably a 1 watt, 15 volt Zener diode.

A MOSFET transistor 34 has its gate 36 connected to the junction 38 between neon light 32 and capacitor 30, its drain 40 connected to one of the electrodes 16, and its source 42 connected to the negative pole of power supply 10. MOSFET transistor 34 may be, for example, an IRF730, rated at 5.5 amps and 400 volts. Current limiting resistors 44, 46, 48 and 50 are 30 mega-ohm, 100 ohm, 1 mega-ohm and 2 mega-ohm resistors respectively, each ¼ watt type.

When switch 18 is turned on, capacitor 24 charges to 300 volts in about 30 seconds. The neon light 20 shows when this has been accomplished. To send pulses to electrode 16, switch 22 is depressed (turned on).

When switch 22 is on, capacitor 28 charges from the current drain from capacitor 24 through resistor 44. Capacitor 28 reaches 70 volts in about ⅓ seconds. When capacitor 28 reaches 70 volts, neon light 32 discharges causing capacitor 28 to discharge through Zener diode 30 to ground. By the appropriate choice of the neon light 32, this occurs in about 0.005 seconds. For a different pulse length, a different neon light 32 should be chosen.

While neon light 32 discharges, junction 38 rises to 15 volts, the discharge level of the Zener diode. This voltage is then passed to the gate 36 of transistor 34 and causes the transistor 34 to turn on during the discharge time of neon light 32. While the transistor 34 is turned on, current is allowed to pass through the drain 40 and source 42, resulting in a pulse of about 300 volts passing through the electrodes 16 in about 0.005 seconds. When capacitor 28 is discharged, it begins to charge again and the process repeats itself, in this case about three times per second.

The pulse generator 12 described here results in a wave form of the type shown in FIG. 1 where t=0.005 seconds, V=300 volts, f=3 Hertz and I=0.34 amps (in moist soil).

To prevent shocks across the electrodes 16 from blowing out the transistor 34, it may be desirable to include a 50 ohm resistor (not shown) in series with the electrodes 16. Other ways of limiting the current passing through the transistor 34 may also be used, for example, by using a lower voltage Zener diode 30 to reduce the voltage at the gate 36 of transistor 40.

In operation, the electrodes 16 are placed in moist soil about 30 cm. apart. The power supply 10 is turned on and the switch 22 turned on once neon light 20 shows the power supply 10 is charged. The blinking of neon light 32 as it discharges indicates that the circuit is working.

The power used allows for greater portability than achieved before for such a device. In addition, because of the low power, any shock received from this device will be far less likely to injure a person than if a storage battery or household power source were used. The applicants have found that using "C" size batteries result in a mild shock without burning the skin. In addition, in practice the applicants have found that the device tends to discriminate in favour of large worms, which is believed (although we are not certain) to be caused by the voltage divider effect of large worms: the worm tends to be affected by more of the current. The rest period between the pulses allows time for the earth worms to reach the surface of soil, and, if the rest period is not too long, prevents them from escaping deeper into the soil.

In addition, since low power is used the earthworms removed are still "live" and not, as is the case with high power devices, severely damaged.

Different pulse characteristics may be obtained by a different choice of components in the pulse generator 12. For example, a different photoflash power supply may be used to obtain a different voltage (with appropriate modifications to the circuit components as required).

We claim:

1. Portable apparatus for causing earthworms to come to the surface of soil comprising;
    (a) a power supply;
    (b) circuit means connected to said power supply for producing electric pulses having the following characteristics:
        average power, P, during each pulse between 10 watts and 500 watts;
        duration, t, of each pulse between 0.1 second and 0.001 second; and
        frequency, f, of the pulses between 0.5 Hertz and 10.0 Hertz;
        each of P, f and t being chosen so that the product of P, f and t is maintained between 0.1 watts and 10 watts;
    (c) and a pair of electrodes connected to said circuit means for coupling said pulses into said soil.

2. The apparatus of claim 1 in which said circuit means is capable of producing electric pulses having the following characteristics:
    average power, P, during each pulse between 10 watts and 500 watts;
    duration, t, during each pulse between 0.1 second and 0.001 second; and
    frequency, f, of the pulses between 0.5 Hertz and 10.0 Hertz;
    each of P, f and t being chosen so that the product of P, f and t is maintained between 0.5 watts and 5 watts.

3. The apparatus of claim 1 in which said circuit means is capable of producing pulses having the following characteristics:
    average power, P, during each pulse between 30 watts and 300 watts;
    duration, t, of each pulse between 0.01 second and 0.004 second; and
    frequency, f, of the pulses between 1 Hertz and 4 Hertz;
    each of P, f and t being chosen so that the product of P, f and t is maintained between 0.5 watts and 5 watts.

4. The apparatus of claim 1, 2 or 3 in which the power supply is a photoflash power supply and said circuit means includes means for chopping the power provided by the power supply and for stepping up the voltage of the power supply.

5. A method of causing earthworms to come to the surface of soil comprising applying to the soil electric pulses having the following characteristics:
    average power, P, during each pulse between 10 watts and 500 watts;
    duration, t, of each pulse between 0.1 second and 0.001 second; and
    frequency, f, of the pulses between 0.5 Hertz and 10.0 Hertz;
    each of P, f and t being chosen so that the product of P, f and t is maintained between 0.1 watts and 10 watts.

6. The method of claim 5 in which said pulses are produced by a power supply and a circuit means connected to the power supply for chopping the power provided by the power supply and for stepping up the voltage of the power supply.

7. The method of claim 5 in which said pulses have uniform polarity and a square waveform.

8. The method of claim 5 in which the power supply for producing said pulses is a photoflash power supply.

9. A method of causing earthworms to come to the surface of soil comprising applying to the soil electric pulses having the following characteristics:
    average power, P, during each pulse between 10 watts and 500 watts;
    duration, t, of each pulse between 0.1 and 0.001 seconds; and
    frequency, f, of the pulses between 0.5 Hertz and 10 Hertz
    each of P, f and t being chosen so that the product of P, f and t is maintained between 0.5 watts and 5 watts.

10. The method of claim 9 in which said pulses are produced by a power supply and a circuit means connected to the power supply for chopping the power provided by the power supply and for stepping up the voltage of the power supply.

11. The method of claim 10 in which said pulses have a uniform polarity and a square waveform.

12. The method of claim 10 in which the power supply for producing said pulses is a photoflash power supply.

13. A method of causing earthworms to come to the surface of soil comprising applying to the soil electric pulses having the following characteristics;

average power, P, during each pulse between 30 watts and 300 watts;

duration, t, of each pulse between 0.01 second and 0.004 second; and frequency, f of the pulses between 1 Hertz and 4 Hertz;

each of P, f and t being chosen so that the product of P, f and t is maintained between 0.5 watts and 5 watts.

14. The method of claim 13 in which said pulses are produced by a power supply and a circuit means connected to the power supply for chopping the power provided by the power supply and for stepping up the voltage of the power supply.

15. The method of claim 14 in which said pulses have uniform polarity and a square waveform.

16. The method of claim 15 in which the power supply for producing said pulses is a photoflash power supply.

* * * * *